(12) United States Patent
Dean

(10) Patent No.: US 8,076,266 B2
(45) Date of Patent: *Dec. 13, 2011

(54) UREA PHOSPHITE FUNGICIDE

(75) Inventor: Frank William Dean, Spring, TX (US)

(73) Assignee: Lidochem, Inc., Hazlet, NJ (US)

( * ) Notice: Subject to any disclaimer, the term of this patent is extended or adjusted under 35 U.S.C. 154(b) by 486 days.

This patent is subject to a terminal disclaimer.

(21) Appl. No.: 12/316,190

(22) Filed: Dec. 10, 2008

(65) Prior Publication Data

US 2009/0099021 A1    Apr. 16, 2009

Related U.S. Application Data

(63) Continuation-in-part of application No. 11/228,648, filed on Sep. 17, 2005.

(60) Provisional application No. 60/610,747, filed on Sep. 17, 2004.

(51) Int. Cl.
*A01N 25/26* (2006.01)
*A01N 57/00* (2006.01)

(52) U.S. Cl. .......... 504/100; 504/127; 504/194

(58) Field of Classification Search .......... None
See application file for complete search history.

(56) References Cited

FOREIGN PATENT DOCUMENTS

RU    2191111    *    1/2001

* cited by examiner

*Primary Examiner* — Alton Pryor
(74) *Attorney, Agent, or Firm* — Karen B. Tripp

(57) ABSTRACT

Urea Phosphite is a new composition of matter useful as a fertilizer and as a fungicide. It is made by reacting phosphorous acid with urea. Urea Phosphite is characterized by being a liquid produced in an unprocessed reaction, and by having phosphite as a phosphorus source and urea as a nitrogen source. The reaction products may be separated, blended with an admix and spray dried, or dissolved in water. This new composition of matter avoids the pitfalls of pathological acerbation reported with the use of phosphite fertilizers and fungicides. When blended with an admix, this new composition is also believed to have the ability to break dormancy in temperate fruiting crops.

14 Claims, No Drawings

UREA PHOSPHITE FUNGICIDE

RELATED APPLICATIONS

This application is a continuation-in-part of U.S. patent application Ser. No. 11/228,648, filed Sep. 17, 2005, pending, which claims priority to U.S. Provisional Patent Application No. 60/610,747 filed Sep. 17, 2004, by Frank William Dean, entitled "Urea Phosphite."

BACKGROUND OF THE INVENTION

1. Field of the Invention

This invention relates to new chemical compositions of matter having utility as industrial chemicals, fertilizers, and, fungicides. This invention particularly relates to phosphite compositions. It has been found that the new composition of matter of the present invention avoids the pitfalls of pathological acerbation reported with the use of phosphite fertilizers and fungicides; therefore, urea phosphite may be used as a lone phosphite source, or, combined with other acerbating phosphites, and avoid the eiphytotic outbreak cited by Taylor in U.S. Pat. No. 5,736,164. It has also been found that this composition blended with an admix may have the ability to break dormancy in temperate fruiting crops.

2. Brief Description of Relevant Art

In greenhouses, nurseries, and gardens, or other intensive horticulture environments, best results are attained when fertilizers and pesticides are carefully delivered to the soil or to growing plants. Many growers choose to utilize blended high analysis water-soluble fertilizers and fungicides. These fertilizers and fungicides are marketed as liquids or solids, which are dissolved or diluted, to prepare concentrated stock solutions; these fertilizer/fungicide solutions may again then be diluted by irrigation water by means of proportional or injection devices.

In agriculture most excellent results are also achieved when fertilizers and pesticides are carefully delivered to the soil or to growing plants. Many growers choose to utilize blended high analysis water-soluble fertilizers and fungicides. These fertilizers and fungicides are marketed either as solids or liquids; the fertilizers and/or fungicides are dissolved in spray tanks for foliar applications, or are used to prepare concentrated stock solutions for ground application.

It is also desired that fertilizer and fungicide formulations have good long-term stability as stock solutions so as not to form precipitates, which can clog spray rigs, proportioners, and irrigation lines. This has been a limitation with known water-soluble fertilizer and fungicide formulations commercially available.

Mineral salts are important nutrients which are called for in many plant nutrition formulations, but, mineral salts cannot be used together with conventional phosphorus sources. For instance, ammonium and potassium phosphates in solution alter pH and do not allow adequate solubility to mineral salt ions, giving rise to precipitation of the mineral salts in the stock solution which clog equipment.

Potassium phosphate or sodium phosphate can be used as soluble phosphorous sources but these can be expensive or not conducive to plant growth. Phosphoric acid can be used but it is a liquid, hazardous to handle, and toxic to plants. Therefore, a grower wishing to fertilize with both mineral salts and phosphorus, without resorting to the use of an alkali metal or ammonium phosphate, or, liquid phosphoric acid, will need to inject these compounds separately.

Additionally, the use of chelated trace nutrients has been widely postulated in order to keep these trace nutrients dissolved in stock solutions that contain the ammonium and potassium phosphates. If non-chelated mineral salts are added with the conventional phosphorus sources, the phosphate minerals will precipitate from the solution. Chelated minerals increase the cost of the fertilizer and fungicide formulations.

U.S. Pat. No. 5,736,164 to Taylor teaches a phenomenon called Pathological Acerbation, as follows:

In accordance with this development of the present invention, however, it has recently been discovered that phosphonates exacerbate the non-target Ascomycete fungi, producing an eiphytotic outbreak of much greater magnitude than the infections occurring without phosphonate treatment. This phenomenon is known as pathological acerbation.

SUMMARY OF THE INVENTION

The present invention concerns new fertilizer and/or fungicide compositions; I have found liquid and solid fertilizer and fungicide compositions useful for preparing aqueous solutions and fertilizer solids for plant nutrition and plant fungicides.

The present invention employs Urea Phosphite as a liquid for fertilizer and fungicide formulations. Until now Urea Phosphite was an unknown material.

Urea Phosphite is an improved concentrated material for use as a fertilizer and fungicide. Urea phosphite dissolves completely in water or forms solids in the presence of other materials, to give a nitrogen and phosphorus-containing substance. This fertilizer and/or fungicide is characterized by being a liquid produced in an unprocessed reaction, and by having phosphite as a phosphorus source and urea as a nitrogen source.

The present invention generally relates to a new composition of matter and to uses for that composition. These uses include agricultural, industrial, and, commercial uses of these compounds. More specifically, the present invention is directed to the reaction product formed by reacting phosphorous acid crystals (a solid) with urea (a solid) to form the new compound Urea Phosphite (a concentrated liquid), to methods for conducting that reaction, and, to uses of the reaction product. The present invention is directed to uses for new compositions of matter comprising the reaction product of a phosphorous acid and a urea, including substituted ureas such as the thioureas and phenylureas. The reaction products may be separated, blended with an admix and spray dried, or, dissolved in water.

Urea, being approximately 46% by weight nitrogen, has long been preferred as a nitrogen source for fertilizing soils to stimulate plant growth. Phosphorous acid, being approximately 86.5% by weight $P_2O_5$, and its salts has been used as a fungicide and a fertilizer. Urea, phosphorus acid and urea phosphite are compared in Table I below.

TABLE I

| Compound | MW | MP ° C. | Solubility (g/100 ml) | Density |
|---|---|---|---|---|
| Phosphorous acid | 82 | 73.6 | 309 | 1.651 |
| Urea | 60.06 | 135 | 100 | 1.32 |
| Urea phosphite | 142.06 | 0 | Infinite | 1.4 |

Urea Phosphite, $CO(NH_2)_2 \cdot H_3PO_3$ is believed to have the following chemical structure:

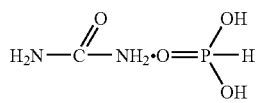

Often time's fertilizers and fungicides are used with buffers. The buffering prevents the alkaline hydrolysis of insecticides, fungicides, and, herbicides, therefore, insuring greater efficacy to their pesticide applications. Urea Phosphite will serve as an excellent low pH buffer thereby protecting the applicators pesticide investment.

It has been recently observed the acerbation of ascomyceties does not occur with the use of this new composition of matter. Indeed, it has been found when other products reported to cause the acerbation of ascomyceties are used in combination with the urea phosphite the problem does not occur.

In another area of discovery it has been found the use of urea phosphite blended with an admix will induce a break of dormancy in temperate vines and trees. The application of urea phosphite to a dormant crop will induce an even bud break. An early even bud break enhances the chance for earlier flowering, earlier photosynthesis, and, potentially greater harvest.

The practice of initiating bud break is important. If there has not been enough "cold hours" there will not be an even dormancy break or flower production. If there are not enough cold hours during the winter season the flowering of a fruit-bearing tree is minimal, the flowering period is spread out and the crop frequently yields a smaller harvest.

Chemicals like the poisonous Cyanamid have in the past been used to initiate the breaking of dormancy. However, as populations encroach on farmland, populations demand safer food stocks, and, growers become better stewards of the land, the entire marketplace is demanding environmentally friendly growing practices. The use of urea phosphite promotes the environmentally friendly growing goals of people friendly, plant friendly, and land friendly chemical applications.

DETAILED DESCRIPTION OF PREFERRED EMBODIMENTS

Urea undergoes a reaction with phosphorous acids. These products have not been known until now. The agricultural industry has felt the need for ways to protect plants from fungal attack, to improve early seedling vigor, and to increase plant biomass, all resulting in improved yield and quality. There has been a long felt but unfulfilled need in the industry for improved methods for achieving these goals. The present invention works to solve those needs.

Being a clear colorless liquid with low moisture content this invention allows producers to deliver high analysis and concentrated fertilizers and fungicides. When the urea phosphite is compared to other liquid products the urea phosphite will be substantially less expensive to manufacture, transport, ship, store and warehouse, package, and deliver to end-users than many if not all prior art products.

In a preferred embodiment phosphorous acid is reacted with urea in a molar ratio of about 1:1 to produce Urea Phosphite. While the reaction may be conducted at any temperature between about 15° C. and about 140° C., it is preferably conducted within the range of about 15° C. to about 100° C. The reaction may conveniently be conducted at room temperature. Preferably the reactants are stirred until the reaction mixture is clear. The liquid reaction product will form and may be dissolved in water, packaged as is, or blended with an admix to produce liquids and solids, or further compounded/reacted with an admix and spray dried.

The reaction product of the present invention, most preferably Urea Phosphite, will be found to produce enhanced growth in plants when used in a variety of ways. The reaction product Urea Phosphite will produce enhanced growth when applied to seeds or soil prior to or at planting, when applied to the soil surrounding the plant at or after planting or when applied to the foliage of the plant. Alternatively, a solution or dry matter of urea phosphite may be applied to the soil surrounding the seed and/or emerging plant. All application methods will deliver fertilization and fungal protection.

When applied to the foliage, those skilled in the art may include a conventional admix in the solution to improve the retention of reaction product on the leaves so that the plant may more readily absorb it.

Solutions containing mineral salts or non-chelated micronutrient trace metals, such as: calcium, magnesium, cobalt, iron, manganese, copper, boron, zinc and molybdenum, may be made available to the plant by dissolving them completely in water with urea phosphite without precipitate formation initially or upon prolonged standing, such as for 24 hours or longer. In one embodiment, this invention provides a mineral salts-containing solid complex fertilizer and fungicide, which dissolves completely in water to give a water-based precipitate-free, stable aqueous stock solution. A liquid fertilizer and/or fungicide containing Urea Phosphite will provide phosphite as a phosphorus, and, urea as a nitrogen source for plant protection and nutrition.

In another embodiment, this invention provides a trace metal-containing solid blended fertilizer and/or fungicide that dissolve completely in water to give a water-based, precipitate free, stable aqueous stock solution.

In another embodiment, this invention provides a fertilizer and/or fungicide comprising or containing urea phosphite as a phosphorus source and chelated, partially chelated, complexed, or non-chelated micronutrient trace metal nitrates, chlorides, carbonates, oxides or sulfate salts. This material may contain magnesium and/or calcium as well. It also may contain any mineral salt.

In still another embodiment, this invention provides a method for preparing a stable phosphorus-containing fertilizer and fungicide with an admix. Please see the text below for the Discussion of Possible Admixes. For aqueous stock solutions this method involves blending or adding a fertilizer and fungicide admix to Urea Phosphite. For blended liquid and solid fertilizer and fungicide products this method includes compounding or blending an admix with the liquid urea phosphite. These same general processes can be used to prepare a non-chelated mineral salt blended with the urea phosphite containing fertilizer and fungicide.

The inclusion of urea Phosphite in a dry blended mixture of nutrient sources which include calcium salts, and/or, magnesium with or without trace metals such as iron and the like in non-chelated forms such as nitrates and/or sulfates offers several advantages. For one, the Urea Phosphite establishes a low pH condition when the blended mixture is added to water to make a concentrated stock solution. A stock solution pH in the range of 0 to 2 may be achieved. This low solution pH maintains solubility and clarity of the concentrated stock solution. Urea Phosphite, by the effect it has on solution pH, prevents the formation of mineral salts of phosphite that are not soluble.

Similarly, the low pH helps prevent mineral salts from precipitating in the presence of sulfate ions, which may be present. Therefore, when Urea Phosphite is used as a phosphorus source, it will make possible the inclusion of phosphorus and the mineral salts in one compound fertilizer and/or fungicide, without the use of chelates, or the disadvantage of a precipitate forming.

This allows the end user to prepare and apply a complete fungicidal and/or nutrient solution using one stock solution and utilizing one injector. It also makes possible the inclusion of non-chelated trace nutrients into phosphorous-containing nutrient solutions without precipitation. It also allows the fertilizer and fungicide solution to have an increased acidifying effect on the growing medium if needed. In summary, the advantages of using Urea Phosphite as a phosphorus source in a compound fertilizer and/or fungicide are:

- The ability to purchase, prepare and apply a complete fungicidal and/or nutrient solution with one stock solution without fear of pathological acerbation.
- The ability to use non-chelated mineral salts without a reduction in solubility in the stock solution as is observed using conventional dry phosphorus sources.
- The ability to formulate acidic fertilizers and/or fungicides that are sold as dry solids or liquids and thus are less hazardous to the end user than liquid phosphoric acid-based materials.
- The ability to enhance the breaking of dormancy in temperate vine and tree crops The fertilizer and fungicide compositions of this invention contain Urea Phosphite. The amount of Urea Phosphite will vary depending upon the nitrogen and phosphorous analysis desired for the formulated composition. Typically, the Urea Phosphite is used with an Admix—this includes other nutrient sources. Since Urea Phosphite contributes nitrogen as well as phosphorus in a stoichiometric ratio to the fertilizer and fungicide mix it may be necessary to add additional potassium, phosphorus, and nitrogen sources to alter the ratio provided by Urea Phosphite alone.

The molar ratios between the urea and phosphorous acid are between 2:1 and 1:2; an excess of either material may be present without interfering in the direct preparation of the liquid Urea Phosphite.

Of course, any suitable mixer system can be used and it is not necessary that the mixing be done simultaneously with the onward conveying; the reactants may dwell in the mixer for a time and the entire product then be discharged from the mixer at once.

In order to improve the free-flowing properties of the Urea Phosphite liquid, a common anti-caking agent such as amorphous silica, bentonite, flour, etc., may be added. The amount of the anti-caking agent is in the usual range utilized for this purpose such as between 1.50-3% by weight.

The process is very simple to carry out; after mixing phosphorous acid with the urea, the reaction system may be heated in view of the endothermic reaction, which takes place. The reaction is accomplished once the blend is clear and colorless and liquid Urea Phosphite formed in the reaction vessel is ready for use without any further operation.

The urea to be used as a starting material in the reaction according to the invention may be any urea form commercially available such as prills, crystals, or diluted liquids. The phosphorous acid to be used as a starting material in the reaction according to the invention may be any form commercially available such as crystals, or diluted liquids.

When the urea phosphite is for fertilizer or fungicide use, desired micronutrients such as Mg, Co, Fe, Zn, Cu, Mn, etc., may be incorporated in the initial phosphorous acid prior to the reaction with the solid urea without interfering with the course of reaction. This is an additional advantage where a reliable dosage of micronutrients is not possible.

If desired to obtain compounds with a higher ratio of N:P or N:P:K for fertilizers, the urea phosphite may be transformed into prills by an admix. It can also be used in various compound fertilizers.

A solid product of the invention may contain about 0.01% by weight (total solids) of urea phosphite that, by itself, will contribute about 0.005% weight phosphorous as $P_2O_5$, and about 0.002% weight nitrogen as N. The liquid product can contain up to about 100% by weight of Urea Phosphite that would by itself contribute about 50% weight phosphorus as $P_2O_5$ and about 20% weight nitrogen as N.

Higher P or N assays can be achieved by the addition of phosphorus sources or various nitrogen sources, such as urea, ammonium, or, nitrate sources. In cases where urea phosphite is not the sole phosphorus source, other phosphates such as the potassium phosphates' and ammonium phosphates' can make up the balance. Other sources of phosphite fertilizers/fungicides reported to cause the acerbation of ascomyceties may also be combined with the urea phosphite to avoid the problem of acerbating the ascomycota fungi.

In addition to the phosphorous and nitrogen content the blend may include potassium. Similarly, it may be of advantage to include an admix discussed below. Some of those admixes may include the use and combination of materials noted to cause the acerbation of ascomycete fungi, they include the ammonium ion, organic bases, alkali, alkaline earth, and transition metal salts of phosphites, but, as previously noted, when mixed with Urea Phosphite, do not cause ascerbation of ascomycete fungi. It has also been found this composition blended with an admix may have the ability to break dormancy in temperate fruiting crops.

EXPERIMENTS

The invention may be further understood from the examples below.

EXAMPLE 1

White Crystal Sample—Sample 1

325 grams 70% phosphorous acid solution was blended with 175 grams of urea and heated at temperatures greater then 100° C. where it became fluid syrup. The exothermic reaction between the two reactants started immediately. The reaction mixture was removed from heat and allowed to proceed spontaneously. The reaction mixture became a non-transparent fluid syrup that expelled gas and bubbled from which crystalline material resulted as the reaction cooled.

Because of the faint smell of ammonia, some of the urea is believed to have decomposed and products other than urea phosphite may have also been formed.

EXAMPLE 2

Sample 2

For a mole ratio of 1:1 (phosphorous acid:urea), 57 grams phosphorous acid crystals were blended with 45 grams urea mini-pills and stirred at 80° C. in a covered container for 1 hour. The blend of 2 solids produced a clear, colorless liquid urea phosphite. The liquid is stable upon heating to 90° C. or cooling to 0° C. the solution has a fertilizer value of 20% N and 50% $P_2O_5$.

EXAMPLE 3

55 grams phosphorous acid crystals were blended with 42 grams urea pills and stirred in a covered container at room temperature. The blend of 2 solids produced a clear, colorless liquid urea phosphite. The liquid is stable upon heating to 90° C. or cooling to 0° C.

EXAMPLE 4

For a mole ratio of 1:2 (phosphorous acid:urea) 55 grams phosphorous acid crystals were blended with 84 grams urea pills and stirred in a covered container. The blend of 2 solids heated to temperatures greater than the melting point of the phosphorous acid (73° C.) and stirred; a clear, colorless liquid Urea Phosphite was formed. The liquid is stable upon heating to 90° C. and crystals formed upon cooling.

EXAMPLE 5

Diammonium phosphate crystals and monopotassium phosphate crystals were blended with urea phosphite liquid to produce a free flowing dry soluble product.

EXAMPLE 6

Sample 3

For a mole ratio of 2:1 (phosphorous acid:urea), 73 grams phosphorous acid crystals were blended with 27 grams urea pills and stirred in a covered container at room temperature. The blend of 2 solids produced a clear, colorless liquid Urea Phosphite.

EXAMPLE 7

For a mole ratio of 1:1 (phosphorous acid:urea) 114 grams phosphorous acid crystals were blended with 86 grams urea pills and stirred at 80° C. in a covered container for 1 hour. The blend of 2 solids produced a clear, colorless liquid Urea Phosphite. From this 50 g of the Urea Phosphite was blended with 100 ml of water, and 30 grams of calcium nitrate was added. The blend produced a clear 8-14-0, 3% Ca liquid fertilizer or fungicide with soluble phosphorus, nitrogen and calcium available for plant nutrition. Although the calcium was not chelated, the calcium did not precipitate in the presence of the phosphorus compound.

EXAMPLE 8

50 g of Urea Phosphite liquid was blended with 100 ml of water and 30 grams of magnesium nitrate was added at room temperature. The blend produced a clear 7-14-0, 2.7% Mg liquid fertilizer or fungicide with soluble phosphorus, nitrogen and magnesium available for plant nutrition. Although the magnesium was not chelated, the magnesium did not precipitate in the presence of the phosphorus compound.

EXAMPLE 9

To demonstrate the fungicidal qualities of Urea Phosphite a trial was set up to measure it's effectiveness against Downey Mildew fungus on lettuce. After two applications the following ratings set forth in Table II were found:

TABLE II

DOWNEY MILDEW LETTUCE TRIAL
(Rating scale is 1 to 10; with 10 being no control of the fungal disease)

| Product | Mean of 4 Replications | Ranking |
|---|---|---|
| 1 (potassium phosphite) | 4.62 | 3 |
| 2 (potassium phosphite) | 4.81 | 4 |
| Urea Phosphite | 3.93 | 1 |
| Aliette ® (aluminum tris ethyl phosphonate) | 4 | 2 |
| Control | 6.25 | 5 |

Aliette ® is a trademark of Rhone-Poulenc, France.

There was no indication of pathological acerbation where urea phosphite was applied.

EXAMPLE 10

A dry soluble blend of fertilizers, micronutrients, plant growth regulators, carbon sources, chelating agents, surfactants, and seaplant extract was produced as itemized below in Table III.

TABLE III

Fertilizer Analysis of 7-24-17 with 2% Mn & 0.5% B

| | Batch Size: | |
|---|---|---|
| Ingredients and order of addition | 1,000 % | Grams Grams |
| Manganese sulfate | 6.25% | 63 |
| EDTA ACID (chelating agent) | 11.10% | 111 |
| Mono Potassium Phosphate (0-52-30) | 25.00% | 250 |
| Diammonium Phosphate | 22.50% | 225 |
| Potassium Chloride | 15.0% | 150 |
| Siponate-50 (anti caking Agent) | 4.00% | 40 |
| Boric acid | 2.90% | 29 |
| Table sugar | 2.00% | 20 |
| Acadian seaplant extract (Extracted from *Ascophyllum nodosum*, comprising short-chain carbohydrates (such as β-glucans), a range of specialized amino acids (betaines), plus regular amino acids, a low level mix of over 60 chelated micro-and macronutrients, and organic compounds) | 0.50% | 5 |
| Growth regulators and surfactants (including Gibberillic acid, 6-Benzylamino Purine, Indole-3-butyric acid, alkyl phenol ethoxyaltes, Phosphate Esters, and antifoaming agents.) | 1.25% | 13 |
| Urea Phosphite liquid | 9.50% | 95 |
| Total | 100.00% | 1,000 |

The liquid Urea Phosphite was poured over the dry fertilizer blend. This blend is suitable for sale and distribution as a dry soluble fertilizer—fungicide combination. That fact that Urea Phosphite as a liquid can be used as an ingredient in a dry soluble composition or compound, with free flowing capabilities, demonstrates the uniqueness of Urea Phosphite. If another liquid fungicide or fertilizer material known in the prior art had been used, the entire blend would have turned into a solid mass not suitable for packaging and distribution as a dry soluble fertilizer. Also, if a solid compacted material is needed to produce a slow release fertilizer/fungicide, removing the anticaking agent from this blend comprising Urea Phosphite would fulfill this need.

EXAMPLE 11

A liquid blend of water, urea phosphite, calcium ammonium nitrate (CAN 17) and a surfactant (S233) were tested to break dormancy. The application was made in Spring on February 1-2. During the growing season the following observations were made:

Background

Many acres of cherries are grown throughout Kern Co. California. On average, cherries require upwards of 800 or more chill hours in order for normal dormancy breaking to take place. During a typical year it is rare to have this many chill hours accumulate in this portion of the state. When there are inadequate chill hours built up during the winter months, uniform dormancy breaking can be severely diminished resulting in sporadic fruit development and maturation. The market for cherries in Kern Co. is very short and very early (late April to early May). The crop is not harvestable after this time due to competition from northern California and the Pacific Northwest. In order to profitably produce cherries in this area, growers have used a hydrogen cyanimide product which permits the breaking of dormancy with far fewer chill hours (~500) resulting in a more uniform and compressed bloom leading to improved yields. Hydrogen cyanimide is a highly toxic chemical both on people and the environment and in 2006 new regulations were put in place increasing the buffer zone from any surface water to 900' from 300'. With this new regulation many growers were forced to look for an alternative for dormancy breaking. Many different products have been used in the past with limited success.

Test Methods

The trial was conducted on a four-year-old block of cherries ("Tulare" and "Brooks" varieties). Plots consisted of 4 rows totaling approximately 1.6 acres in size each. Treatments were applied using a commercial airblast sprayer at a rate of 100 gallons per acre. Treatments are listed in Table IV. Treatments 1 and 2 were applied on Feb. 1, 2007 and treatment 3 was applied on Feb. 2. Ten randomly selected trees, from each treatment, were later hand picked of all fruit and sorted based on maturity (Mature=Red or Maroon; not Mature=yellow, straw, pale red). Total weights were obtained from each tree and analyzed.

TABLE IV

| Treatment | Product | Rate |
|---|---|---|
| 1 | CAN-17 + Urea phosphite 44 | 25 gal/A + 2 qts/A |
| 2 | CAN-17 + S 233 | 25 gal/A + 25 oz/A |
| 3 | CAN-17 + Urea phosphite 44 + S 233 | 25 gal/A + 2 qts/A + 25 oz/A |

Results:

About midway through bloom, the Treatment 3 trees appeared to have much more uniform budbreak than the other treatments. Upon completion of bloom, when the trees began to leaf out, it became obvious that this treatment stood out from the rest. Typical of cherries grown in this area in the absence of hydrogen cyanimide, budbreak occured to a greater extent on the upper and lower parts of the tree with a distinct reduction in growth from the mid portions of the tree. However, in the case of Treatment 3, one could see very uniform growth from top to bottom on all trees. Even more surprisingly, the "Tulare" variety which is usually more variable than the "Brooks" variety, had just as even a budbreak as the "Brooks" variety.

Final yields (Table V) are given as the average weight, in pounds, per tree from each treatment in this study. Also included is the average weight of mature red berries per tree for each treatment. Treatment 3 (CAN 17+Urea phosphite 44+S233) yielded the highest total weight of fruit and the most mature fruit in this study. Without wishing to be limited by theory, it is believed that the nitrogen from the CAN 17 was introduced into the woody tissues more efficiently with the S233 (surfactant penetrant) and was transported throughout the tree rapidly with the Urea phosphite 44 (14-44 Urea Phosphite). In other studies, treatments which included Urea phosphite 44 and S233 have been shown to improve the uptake and effectiveness of fertilizers and pesticides.

TABLE V

Average yields (lbs/tree) of fruit per tree.

| Treatment | Product | Total | Red |
|---|---|---|---|
| 1 | CAN-17 + Urea phosphite 44 | 2.81 | 0.97 |
| 2 | CAN-17 + S 233 | 2.80 | 1.44 |
| 3 | CAN-17 + Urea phosphite 44 + S 233 | 5.41 | 4.82 |

It was found that the flowering in Treatment 3 had greater uniformity than the other treatments, the appearance of leaves and photosynthesis started at an earlier date, and the ending crop yield was greater. It was also found that there was no hint of pathological acerbation for any of the treatments.

Discussion of Possible Components for Admixes:

For their practical application, the Urea Phosphite compounds according to this invention are rarely used on their own. Instead they generally form part of formulations which also comprise a support and/or a surfactant in addition to active materials In the context of the invention, a support is an organic or mineral, natural or synthetic material with which the active material is associated to facilitate its application, for example, in the case of fertilizer and fungicides, to the plant, to seeds or to soil, or to facilitate its transportation or handling. The support can be solid (e.g, clays, natural or synthetic silicates, resins, waxes, solid fertilizer and fungicides) or fluid (e.g., water, alcohols, ketones, petroleum fractions, chlorinated hydrocarbons, liquefied gases, liquid fertilizer and fungicides).

The surfactant can be an ionic or non-ionic emulsifier, dispersant or wetting agent such as, for example, salts of polyacrylic acids and lignin-sulphonic acids, condensates of ethylene oxide with fatty alcohols, fatty acids or fatty amines.

The compositions comprising the compounds of the present invention can be prepared in the form of wettable powders, soluble powders, dusting powders, granulates, solutions, emulsifiable concentrates, emulsions, suspended concentrates and aerosols.

The wettable powders according to the invention can be prepared in such a way that they contain the active material, and they often or typically contain, in addition to a solid support, a wetting agent, a dispersant and, when necessary, one or more stabilizers and/or other additives, such as, for example, penetration agents, adhesives or anti-lumping agents, colorants etc.

Aqueous dispersions and emulsions, such as, for example, compositions comprising the compounds of this invention obtained by diluting with water a wettable powder or an emulsifiable concentrate are also included within the general scope of the invention. These emulsions can be of the water-in-oil type or of the oil-in-water type, and can have a thick consistency resembling that of a "mayonnaise".

The compositions comprising the Urea Phosphite compounds of the present invention can contain other ingredients, for example protective colloids, adhesives or thickeners, thixotropic agents, stabilizers or sequestrants, as well as other active materials. A modest list of examples of possible formulation components for inclusion with the compositions of this invention follows without limitation.

Carbon Skeleton/Energy (CSE) Components:

The supposed function of this component is to supply carbon skeleton for synthesis of proteins and other molecules or to supply energy for metabolism. Water-soluble carbohydrates such as sucrose, fructose, glucose and other di- and monosaccharides are suitable, commonly in the form of molasses or other by-products of food manufacture. Commercially available lignosulfonates, discussed below under the heading "Complexing Agents," are also suitable as a CSE source inasmuch as they commonly contain sugars. A more detailed listing of common CSE components follows, although this list, while extensive, in not intended to be exhaustive or limiting:

CSE Components:

Sugar—mannose, lactose, dextrose, erythrose, fructose, fucose, galactose, glucose, gulose, maltose, polysaccharide, raffinose, ribose, ribulose, rutinose, saccharose, stachyose, trehalose, xylose, xylulose, adonose, amylose, arabinose, fructose phosphate, fucose-p, galactose-p, glucose-p, lactose-p, maltose-p, mannose-p, ribose-p, ribulose-p, xylose-p, xylulose-p, deoxyribose, corn steep liquor, whey, corn sugar, corn syrup, maple syrup, grape sugar, grape syrup, beet sugar, sorghum molasses, cane molasses, mineral salts lignosulfonate sugar alcohol—adonitol, galactitol, glucitol, maltitol, mannitol, mannitol-p, ribitol, sorbitol, sorbitol-p, xylitol xxxx acids—glucuronic acid, a-ketoglutaric acid, galacturonic acid, glutaric acid, gluconic acid, pyruvic acid, poly galacturonic acid, saccharic acid, citric acid, succinic acid, malic acid, oxaloacetic acid, aspartic acid, phosphoglyceric acid, fulvic acid, ulmic acid, humic acid, glutamic acid.

More CSE Components:

Nucleotides and bases—adenosine, adenosine-p, adenosine-p-glucose, uridine, uridine-p, uridine-p-glucose, thymine, thymine-p, cytosine, cytosine-p, guanosine, guanosine-p, guanosine-p-glucose, guanine, guanine-p, NADPH, NADH, FMN, FADH The Macronutrient Components:

The macronutrients are essential to nutrition and growth of plants. The most important macronutrients are N, P and K.

Some example nitrogen compounds are: ammonium nitrate, monoammonium phosphate, ammonium phosphate sulfate, ammonium sulfate, ammonium phosphatenitrate, diammonium phosphate, ammoniated single superphosphate, ammoniated triple superphosphate, nitric phosphates, ammonium chloride, aqua ammonia, ammonia-ammonium nitrate solutions, mineral salts ammonium nitrate, mineral salts nitrate, mineral salts Cyanamid, sodium nitrate, urea, urea-formaldehyde, urea-ammonium nitrate solution, nitrate of soda potash, potassium nitrate, amino acids, proteins, nucleic acids.

Examples of Phosphate sources include: superphosphate (single, double and/or triple), phosphoric acid, ammonium phosphate, ammonium phosphate sulfate, ammonium phosphate nitrate, diammonium phosphate, ammoniated single superphosphate, ammoniated single superphosphate, ammoniated triple superphosphate, nitric phosphates, potassium pyrophosphates, sodium pyrophosphate, nucleic acid phosphates and phosphonic and phosphorous acid derivatives.

The potassium ion for example can be found in: potassium chloride, potassium sulfate, potassium gluconate, sulfate of potash magnesia, potassium carbonate, potassium acetate, potassium citrate, potassium hydroxide, potassium manganate, potassium phosphate, potassium molybdate, potassium thiosulfate, potassium zinc sulfate and the like.

Sources of mineral salts include for example: mineral salts ammonium nitrate, mineral salts nitrate, mineral salts Cyanamid, mineral salts acetate, mineral salts acetylsalicylate, mineral salts borate, mineral salts borogluconate, mineral salts carbonate, mineral salts chloride, mineral salts citrate, mineral salts ferrous citrate, mineral salts glycerophosphate, mineral salts lactate, mineral salts oxide, mineral salts pantothenate, mineral salts propionate, mineral salts saccharate, mineral salts sulfate, mineral salts tartrate and the like.

Magnesium can be found for example in: magnesium oxide, dolomite, magnesium acetate, magnesium benzoate, magnesium bisulfate, magnesium borate, magnesium chloride, magnesium citrate, magnesium nitrate, magnesium phosphate, magnesium salicylate, magnesium sulfate.

Sulfur containing compounds include for example: ammonium sulfate, ammonium phosphate sulfate, mineral salts sulfate, potassium sulfate, magnesium sulfate, sulfuric acid, cobalt sulfate, copper sulfate, ferric sulfate, ferrous sulfate, sulfur, cysteine, methionine and elemental sulfur.

Micronutrient Components:

The most important micronutrients for plants are or comprise: Zn, Fe, Cu, Mn, B, Co, and Mo.

Vitamin/Cofactor Components:

The most important vitamin/cofactor components for plants are folic acid, biotin, pantothenic acid, nicotinic acid, riboflavin and thiamine. More specific examples of these components are listed as follows without limitation: Thiamine—thiamine pyrophosphate, thiamine monophosphate, thiamine disulfide, thiamine mononitrate, thiamine phosphoric acid ester chloride, thiamine phosphoric acid ester phosphate salt, thiamine 1,5 salt, thiamine tri phosphoric acid ester, thiamine tri phosphoric acid salt, yeast, yeast extract; Riboflavin—riboflavin acetyl phosphate, flavin adenine dinucleotide, flavin adenine mononucleotide, riboflavin phosphate, yeast, yeast extract; Nicotinic acid—nicotinic acid adenine dinucleotide, nicotinic acid amide, nicotinic acid benzyl ester, nicotinic acid monoethanolamine salt, yeast, yeast extract, nicotinic acid hydrazide, nicotinic acid hydroxamate, nicotinic acid-N-(hydroxymethyl)amide, nicotinic acid methyl ester, nicotinic acid mononucleotide, nicotinic acid nitrile; Pyridoxine—pyridoxal phosphate, yeast, yeast extract; Folic acid—yeast, yeast extract, folinic acid; Biotin—biotin sulfoxide, yeast, yeast extract, biotin 4-amidobenzoic acid, biotin amidocaproate N-hydroxysuccinimide ester, biotin 6-amidoquinoline, biotin hydrazide, biotin methyl ester, d-biotin-N-hydroxysuccinimide ester, biotin-maleimide, d-biotin p-nitrophenyl ester, biotin propranolol, 5-(N-biotinyl)-3 aminoallyl)-uridine 5'-triphosphate, biotinylated uridine 5'-triphosphate, N-e-biotinyl-lysine; Pantothenic acid—yeast, yeast extract, coenzyme A; Cyanocobalamin—yeast, yeast extract; Phosphatidylcholine-soybean oil, eggs bovine heart, bovine brain, bovine liver, L-a-phosphatidylcholine, B-acetyl-g-O-alkyl, D-a-phosphatidylcholine (PTCh), B-acetyl-g-O-hexadecyl, DL-a-PTCh, B-acetyl-g-O-hexadecyl, L-a-PTCh, B-acetyl-g-O-(octadec-9-cis-enyl), L-a-PTCh, B-arachidonoyl, g-stearoyl, L-a-PTCh, diarachidoyl, L-a-PTCh, dibehenoyl (dibutyroyl, dicaproyl, dicapryloyl, didecanoyl, dielaidoyl, 12 diheptadecanoyl, diheptanoyl), DL-a-PTCh dilauroyl, L-a-PTCh dimyristoyl (dilauroyl, dilinoleoyl, dinonanoyl, dioleoyl, dipentadeconoyl, dipalmitoyl, distearoyl, diundecanoyl, divaleroyl, B-elaidoyl-a-palmitoyl, B-linoleoyl-a-palmitoyl) DL-a-PTCh di-O-hexadecyl (dioleoyl, dipalmitoyl, B—O-methyl-g-O-hexadecyl, B-oleoyl-g-O-hexadecyl, B-palmitoyl-g-O-hexadecyl), D-a-PTCh dipalmitoyl, L-a-PTCh, B—O-methyl-g-O-octadecyl, L-a-PTCh, B—(NBD-aminohexanoyl)-g-palmitoyl, L-a-PTCh, B-oleoyl-g-O- palmitoyl (stearoyl), L-a-PTCh, B-palmitoyl-g-oleoyl, L-a-PTCh, B-palmitoyl-a-(pyren 1-yl) hexanoyl, L-a-PTCh, B(pyren-1-yl)-decanoyl-g-palmitoyl, L-a-PTCh, B-(pyren-1-yl)-hexanoyl-g-palmitoyl, L-a-PTCh, B-stearoyl-g-oleoyl; Inositol—inositol monophosphate, inositol macinate, myo-inositol, epi-inositol, myo-inositol 2,2'anhydro-2-c-hydroxymethyl (2-c-methylene-myoinositol oxide), D-myo-inositol 1,4-bisphosphate, DL-myo-inositol 1,2-cyclic monophosphate, myo-inositol dehydrogenase, myo-inositol hexanicotinate, inositol hexaphosphate, myo-inositol hexasulfate, myo-inositol 2-monophosphate, D-myo-inositol 1-monophosphate, DL-myo-inositol 1-monophosphate, D-myo-inositol triphosphate, scyllo-inositol; PABA—m-aminobenzoic acid, O-aminobenzoic acid, p-aminobenzoic acid butyl ester, PABA ethyl ester, 3-ABA ethyl ester.

Complexing Agents:

The function of this component, particularly in agricultural applications, aside from its proposed use as a carbon skeleton agent, is to solubilize other components of the composition which otherwise may precipitate and become assailable or may immobilize minerals in the soil which might otherwise be unavailable to flora and fauna. Complexing agents such as, for example, citric acid, humic acids, lignosulfonate, etc. serve to tie up ions such as iron and prevent them from forming precipitates. In some cases this complexing is by way of chelation. These agents may form complexes with the following compounds for example: Citric acid; Ca, K, Na and ammonium lignosulfonates, fulvic acid, ulmic acid, humic acid, Katy-J, EDTA, EDDA (ethylenediaminedisuccinic acid), EDDHA, HEDTA, CDTA, PTPA, NTA, MEA, IDS, EDDS, and 4-phenylbutyric acid.

Other complexing agents include for example: Al and its salts; Zn—zinc oxide, zinc acetate, zinc benzoate, zinc chloride, zinc citrate, zinc nitrate, zinc salicylate, ziram; Fe—ferric chloride, ferric citrate, ferric fructose, ferric glycerophosphate, ferric nitrate, ferric oxide (saccharated), ferrous chloride, ferrous citrate ferrous fumarate, ferrous gluconate, ferrous succinate; Mn—manganese acetate, manganese chloride, manganese nitrate, manganese phosphate; Cu—cupric acetate, cupric butyrate, cupric chlorate, cupric chloride, cupric citrate, cupric gluconate, cupric glycollate, cupric nitrate, cupric salicylate, cuprous acetate, cuprous chloride; B—mineral salts borate, potassium borohydride, borax, boron trioxide, potassium borotartrate, potassium tetraborate, sodium borate, sodium borohydride, sodium tetraborate and boric acid; Mo—molybdic acid, mineral salts molybdate, potassium molybdate, sodium molybdate; Co—cobaltic acetate, cobaltous acetate, cobaltous chloride, cobaltous oxalate, cobaltous potassium sulfate, cobaltous sulfate.

Growth Regulators:

Still another component suitable for use in fertilizer and fungicide compositions comprising Urea Phosphite include the following growth regulators. Seaweed extract—kelp extract, Kinetin, Kinetin riboside, benzyladenine, zeatin riboside, zeatin, extract of corn cockle, isopentenyl adenine, dihydrozeatin, indoleacetic acid, phenylacetic acid, IBA, indole ethanol, indole acetaldehyde, indoleacetonitrile, indole derivitives, gibberellins (e.g. GA1, GA2, GA3, GA4, GA7, GA38 etc.) polyamines, monoethanolamine, allopurinol, GA inhibitors, ethylene inducing compounds, ethylene biosynthesis inhibitors, GABA, anticytokinins and antiauxins, ABA inducers and inhibitors. Again, as with the other listings above and below of suitable components that may be used with or in Urea Phosphite fertilizers and fungicides, this listing is without limitation and other known growth regulators not listed herein might also be used.

Gum Components:

The following example gum components may be used in fertilizer and fungicide compositions comprising Urea Phosphite: Xanthan gum—guar gum, gum agar, gum accroides, gum arabic, gum carrageenan, gum damar, gum elemi, gum ghatti, gum guaiac, gum karya, locust bean gum, gum mastic, gum pontianak, gum rosin, gum storax, gum tragacanth/ Microbialstats, Proprionic Acid, Benzoic Acid, Sorbic Acid and Amino Acids.

Further suitable additives that might be used with Urea Phosphite include microbialstats, proprionic acid, benzoic acid, sorbic acid and amino acids.

Buffers

Buffers may also be used with compositions comprising Urea Phosphite. Example buffers include without limitation: phosphate buffer, formate or acetate buffer, AMP buffer, mineral salts tartrate, glycine buffer, phosphate citrate buffer, tris buffer, and ECT.

If desired, a formulation or composition of the present invention may also include beneficial microorganisms. The compositions comprising the compounds of the present invention thus defined may be applied to plants by conventional methods including seed application techniques, as well as foliar methods.

The foregoing description of the invention has been directed in primary part to particular preferred embodiments in accordance with the requirements of the Patent Statutes and for purposes of explanation and illustration. It will be apparent, however, to those skilled in the art that many modifications and changes in the specifically described methods may be made without departing from the true scope and spirit of the invention.

One non-limiting example of such a modification would be the combining of an excess of one reactant to change the mole ratios in creating Urea Phosphite. Such a modification could be practiced by one skilled in the art from the teachings herein, and such practice would be within the true scope and spirit of the invention.

Therefore, the invention is not restricted to the preferred embodiments described and illustrated but covers all modifications, which may fall within the scope of the following claims.

I claim:

1. A method for treating plants infested with fungi comprising providing a fungicide comprising urea phosphite and applying the fungicide to the plants infested with fungi and/or to the soil in which the plants are growing.

2. The method of claim 1 wherein the fungicide further comprises one or more micronutrient trace metals selected from the group consisting of calcium, magnesium, cobalt, iron, manganese, copper, boron, zinc and molybdenum.

3. The method of claim 1 wherein the urea phosphite is prepared by blending phosphorous acid and urea together at a temperature in the range of about 15° C. to about 140° C.

4. The method of claim 3 wherein the urea phosphite is prepared by blending phosphorous acid and urea together at room temperature.

5. The method of claim 1 wherein the fungicide further comprises calcium and/or magnesium salts.

6. A method for avoiding pathological acerbation when applying fungicide in agricultural applications, comprising mixing urea phosphite with the fungicide and applying the mixture to soil, seeds or plants, wherein the pathological acerbation is avoided.

7. The method of claim 6 wherein the mixture further comprises a fertilizer.

8. A method of enhancing breaking of dormancy in deciduous plants comprising providing a dormancy breaking enhancer comprising urea phosphite and applying the enhancer to the plants while the plants are dormant.

9. The method of claim 8 wherein the enhancer further comprises water, calcium ammonium nitrate and a surfactant.

10. A method for treating plant seeds infested with fungi comprising providing a fungicide comprising urea phosphite and applying the fungicide to the plant seeds infested with fungi or to the soil in which the seeds are planted or will be planted.

11. The method of claim 10 wherein the fungicide further comprises one or more micronutrient trace metals selected from the group consisting of calcium, magnesium, cobalt, iron, manganese, copper, boron, zinc and molybdenum.

12. The method of claim 10 wherein the urea phosphite is prepared by blending phosphorous acid and urea together at a temperature in the range of about 15° C. to about 140° C.

13. The method of claim 12 wherein the urea phosphite is prepared by blending phosphorous acid and urea together at room temperature.

14. The method of claim 10 wherein the fungicide further comprises calcium and/or magnesium salts.

* * * * *